United States Patent [19]

Iovanna et al.

[11] Patent Number: 5,834,214
[45] Date of Patent: Nov. 10, 1998

[54] DETECTION OF PANCREATITIS-ASSOCIATED PROTEIN FOR SCREENING FOR CYSTIC FIBROSIS

[75] Inventors: Juan-Lucio Iovanna; Jean-Charles Dagorn, both of Marseilles, France; Volker Keim, Heddesheim, Germany; Jacques Sarles, Gemenos, France

[73] Assignee: Institut National de la Sante et de la Recherche Medicale, Paris, France

[21] Appl. No.: 464,637

[22] PCT Filed: Dec. 23, 1993

[86] PCT No.: PCT/FR93/01299

§ 371 Date: Aug. 30, 1995

§ 102(e) Date: Aug. 30, 1995

[87] PCT Pub. No.: WO94/15218

PCT Pub. Date: Jul. 7, 1994

[30] Foreign Application Priority Data

Dec. 24, 1992 [FR] France ................................. 92 15730

[51] Int. Cl.$^6$ ................................................. G01N 33/53
[52] U.S. Cl. .......................... 435/2.9; 435/7.1; 435/975; 435/331; 435/333; 435/337; 436/518; 436/536; 436/548; 436/811; 530/388.1; 530/388.25; 530/389.1; 530/389.3
[58] Field of Search ............................ 435/7.1, 7.9, 7.94, 435/69.1, 172.2, 975, 331, 333, 337; 436/518, 548, 536, 811; 530/388.1, 389.1, 388.25, 389.3

[56] References Cited

U.S. PATENT DOCUMENTS

| | | | |
|---|---|---|---|
| 4,281,061 | 7/1981 | Zuke et al. .................................. | 435/7.9 |
| 4,322,274 | 3/1982 | Wilson et al. ........................ | 204/180 G |
| 5,436,169 | 7/1995 | Iovanna et al. .......................... | 436/518 |

FOREIGN PATENT DOCUMENTS

WO91/02796 3/1991 WIPO.
WO91/16428 10/1991 WIPO.

OTHER PUBLICATIONS

Iovanna et al., "Pancreatitis–Associated Protein a Promising Candidate for Neonatal Screening of CF," Abstracts, Pediatric Pulmonology, Supplement 9, p. 239, No. 138, Sep. 1993.
Itoh et al, "Cloning and Tissue Specific Expression of CDNAs for the Human and Mouse Homologues of Rat Pancreatitis–Associated Protein (PAP)," Biochim. Biophys. 1172: 184–186, 20 Feb. 1993.
Keim et al., "Fragments of PAP . . . in Serum and Urine of Patients With Acute Pancreatitis," Pancreas 7(6): 744, Nov. 1992.
Keim et al., "Human Pancreas–Associated Protein," J. Clin. Invest. 90(6): 2284–2291, 17 Dec. 1992.
Sahel et al., "Pancreatitis–Associated Protein (PAP–H) Serum Levels After ERCP," Gastroenterology 102(4 Suppl 2): A289, Apr. 1992.
Wood, Southern Medical Journal, vol. 72, No. 2, pp. 189–202 (Feb. 1979).
Keim et al, Gastroenterology, vol. 103, pp. 248–254 (1992).
Farrell et al, Pediatric Pulmonology Supplement, vol. 7, pp. 11–18 (1991).

*Primary Examiner*—Carol A. Spiegel
*Attorney, Agent, or Firm*—Birch, Stewart, Kolasch & Birch, LLP

[57] ABSTRACT

The invention relates to in vitro detection of human pancreatitis-associated protein (hPAP) for the purpose of screening for cystic fibrosis. hPAP is quantitated in a biological sample, preferably blood, and a high value is indicative of pancreatic dysfunction. Immunoassays as rapid, reliable methods for hPAP quantitation are provided as are antibodies for use in the assays and hybridomas for production of monoclonal antibodies preferred for use in the assays.

35 Claims, 3 Drawing Sheets

| | | | | | | | | | | | | |
|---|---|---|---|---|---|---|---|---|---|---|---|---|
| | cgggagagtgactcctgattgcctcctcaagtcgcagacact | | | | | | | | | ATG<br>Met | CTG<br>Leu | 48<br>2 |
| CCT<br>Pro | CCC<br>Pro | ATG<br>Met | GCC<br>Ala | CTG<br>Leu | CCC<br>Pro | AGT<br>Ser | GTA<br>Val | TCT<br>Ser | TGG<br>Trp | ATG<br>Met | CTG<br>Leu | CTT<br>Leu | 87<br>15 |
| TCC<br>Ser | TGC<br>Cys | CTC<br>Leu | ATG<br>Met | CTG<br>Leu | CTG<br>Leu | TCT<br>Ser | CAG<br>Gln | GTT<br>Val | CAA<br>Gln | GGT<br>Gly | GAA<br>Glu | GAA<br>Glu | 126<br>28 |
| CCC<br>Pro | CAG<br>Gln | AGG<br>Arg | GAA<br>Glu | CTG<br>Leu | CCC<br>Pro | TCT<br>Ser | GCA<br>Ala | CGG<br>Arg | ATC<br>Ile | CGC<br>Arg | TGT<br>Cys | CCC<br>Pro | 165<br>41 |
| AAA<br>Lys | GGC<br>Gly | TCC<br>Ser | AAG<br>Lys | GCC<br>Ala | TAT<br>Tyr | GGC<br>Gly | TCC<br>Ser | CAC<br>His | TGC<br>Cys | TAT<br>Tyr | GCC<br>Ala | TTG<br>Leu | 204<br>54 |
| TTT<br>Phe | TTG<br>Leu | TCA<br>Ser | CCA<br>Pro | AAA<br>Lys | TCC<br>Ser | TGG<br>Trp | ACA<br>Thr | GAT<br>Asp | GCA<br>Ala | GAT<br>Asp | CTG<br>Leu | GCC<br>Ala | 243<br>67 |
| TGC<br>Cys | CAG<br>Gln | AAG<br>Lys | CGG<br>Arg | CCC<br>Pro | TCT<br>Ser | GGA<br>Gly | AAC<br>Asn | CTG<br>Leu | GTG<br>Val | TCT<br>Ser | GTG<br>Val | CTC<br>Leu | 282<br>80 |
| AGT<br>Ser | GGG<br>Gly | GCT<br>Ala | GAG<br>Glu | GGA<br>Gly | TCC<br>Ser | TTC<br>Phe | GTG<br>Val | TCC<br>Ser | TCC<br>Ser | CTG<br>Leu | GTG<br>Val | AAG<br>Lys | 321<br>93 |
| AGC<br>Ser | ATT<br>Ile | GGT<br>Gly | AAC<br>Asn | AGC<br>Ser | TAC<br>Tyr | TCA<br>Ser | TAC<br>Tyr | GTC<br>Val | TGG<br>Trp | ATT<br>Ile | GGG<br>Gly | CTC<br>Leu | 360<br>106 |
| CAT<br>His | GAC<br>Asp | CCC<br>Pro | ACA<br>Thr | CAG<br>Gln | GGC<br>Gly | ACC<br>Thr | GAG<br>Glu | CCC<br>Pro | AAT<br>Asn | GGA<br>Gly | GAA<br>Glu | GGT<br>Gly | 399<br>119 |
| TGG<br>Trp | GAG<br>Glu | TGG<br>Trp | AGT<br>Ser | AGC<br>Ser | AGT<br>Ser | GAT<br>Asp | GTG<br>Val | ATG<br>Met | AAT<br>Asn | TAC<br>Tyr | TTT<br>Phe | GCA<br>Ala | 438<br>132 |
| TGG<br>Trp | GAG<br>Glu | AGA<br>Arg | AAT<br>Asn | CCC<br>Pro | TCC<br>Ser | ACC<br>Thr | ATC<br>Ile | TCA<br>Ser | AGC<br>Ser | CCC<br>Pro | GGC<br>Gly | CAC<br>His | 477<br>145 |
| TGT<br>Cys | GCG<br>Ala | AGC<br>Ser | CTG<br>Leu | TCG<br>Ser | AGA<br>Arg | AGC<br>Ser | ACA<br>Thr | GCA<br>Ala | TTT<br>Phe | CTG<br>Leu | AGG<br>Arg | TGG<br>Trp | 516<br>158 |
| AAA<br>Lys | GAT<br>Asp | TAT<br>Tyr | AAC<br>Asn | TGT<br>Cys | AAT<br>Asn | GTG<br>Val | AGG<br>Arg | TTA<br>Leu | CCC<br>Pro | TAT<br>Tyr | GTC<br>Val | TGC<br>Cys | 555<br>171 |
| AAG<br>Lys | TTC<br>Phe | ACT<br>Thr | GAC<br>Asp | tagtgcaggagggaagtcagcagcctgtgttttggt | | | | | | | | | 602<br>175 |
| | gtgcaactcatcatgggcatgagaccagtgtgaggactcaccctggaagaga | | | | | | | | | | | | 654 |
| | atattcgcttaattcccccaacctgaccacctcattcttatctttcttctgt | | | | | | | | | | | | 706 |
| | ttcttcctccccgctagtcatttcagtctcttcattttgtcatacggcctaa | | | | | | | | | | | | 758 |
| | ggctttaaagagc<u>aataaa</u>attttttagtctgcaaaaaaa | | | | | | | | | | | | 797 |

Figure 3

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 797 base pairs
        ( B ) TYPE: nucleic acid
        ( C ) STRANDEDNESS: Not Relevant
        ( D ) TOPOLOGY: Not Relevant ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 43..567
        ( D ) OTHER INFORMATION: /product="human
             pancreatitis- associated protein"
            / note= "see, Fig. 3"

( x i ) SEQUENCE DESCRIPTION: SEQ ID NO:1:

```
CGGGAGAGTG  ACTCCTGATT  GCCTCCTCAA  GTCGCAGACA  CT  ATG  CTG  CCT  CCC          54
                                                    Met  Leu  Pro  Pro
                                                     1

ATG  GCC  CTG  CCC  AGT  GTA  TCT  TGG  ATG  CTG  CTT  TCC  TGC  CTC  ATG  CTG   102
Met  Ala  Leu  Pro  Ser  Val  Ser  Trp  Met  Leu  Leu  Ser  Cys  Leu  Met  Leu
 5                   10                   15                        20

CTG  TCT  CAG  GTT  CAA  GGT  GAA  GAA  CCC  CAG  AGG  GAA  CTG  CCC  TCT  GCA   150
Leu  Ser  Gln  Val  Gln  Gly  Glu  Glu  Pro  Gln  Arg  Glu  Leu  Pro  Ser  Ala
                    25                        30                       35

CGG  ATC  CGC  TGT  CCC  AAA  GGC  TCC  AAG  GCC  TAT  GGC  TCC  CAC  TGC  TAT   198
Arg  Ile  Arg  Cys  Pro  Lys  Gly  Ser  Lys  Ala  Tyr  Gly  Ser  His  Cys  Tyr
               40                        45                       50

GCC  TTG  TTT  TTG  TCA  CCA  AAA  TCC  TGG  ACA  GAT  GCA  GAT  CTG  GCC  TGC   246
Ala  Leu  Phe  Leu  Ser  Pro  Lys  Ser  Trp  Thr  Asp  Ala  Asp  Leu  Ala  Cys
          55                        60                       65

CAG  AAG  CGG  CCC  TCT  GGA  AAC  CTG  GTG  TCT  GTG  CTC  AGT  GGG  GCT  GAG   294
Gln  Lys  Arg  Pro  Ser  Gly  Asn  Leu  Val  Ser  Val  Leu  Ser  Gly  Ala  Glu
     70                        75                       80

GGA  TCC  TTC  GTG  TCC  TCC  CTG  GTG  AAG  AGC  ATT  GGT  AAC  AGC  TAC  TCA   342
Gly  Ser  Phe  Val  Ser  Ser  Leu  Val  Lys  Ser  Ile  Gly  Asn  Ser  Tyr  Ser
 85                        90                       95                      100

TAC  GTC  TGG  ATT  GGG  CTC  CAT  GAC  CCC  ACA  CAG  GGC  ACC  GAG  CCC  AAT   390
Tyr  Val  Trp  Ile  Gly  Leu  His  Asp  Pro  Thr  Gln  Gly  Thr  Glu  Pro  Asn
                    105                       110                      115
```

-continued

```
GGA  GAA  GGT  TGG  GAG  TGG  AGT  AGC  AGT  GAT  GTG  ATG  AAT  TAC  TTT  GCA              438
Gly  Glu  Gly  Trp  Glu  Trp  Ser  Ser  Ser  Asp  Val  Met  Asn  Tyr  Phe  Ala
               120                      125                      130

TGG  GAG  AGA  AAT  CCC  TCC  ACC  ATC  TCA  AGC  CCC  GGC  CAC  TGT  GCG  AGC              486
Trp  Glu  Arg  Asn  Pro  Ser  Thr  Ile  Ser  Ser  Pro  Gly  His  Cys  Ala  Ser
          135                      140                      145

CTG  TCG  AGA  AGC  ACA  GCA  TTT  CTG  AGG  TGG  AAA  GAT  TAT  AAC  TGT  AAT              534
Leu  Ser  Arg  Ser  Thr  Ala  Phe  Leu  Arg  Trp  Lys  Asp  Tyr  Asn  Cys  Asn
     150                      155                      160

GTG  AGG  TTA  CCC  TAT  GTC  TGC  AAG  TTC  ACT  GAC  TAGTGCAGGA   GGGAAGTCAG              587
Val  Arg  Leu  Pro  Tyr  Val  Cys  Lys  Phe  Thr  Asp
165                      170                      175

CAGCCTGTGT  TTGGTGTGCA  ACTCATCATG  GGCATGAGAC  CAGTGTGAGG  ACTCACCCTG                      647

GAAGAGAATA  TTCGCTTAAT  TCCCCCAACC  TGACCACCTC  ATTCTTATCT  TTCTTCTGTT                      707

TCTTCCTCCC  CGCTAGTCAT  TTCAGTCTCT  TCATTTTGTC  ATACGGCCTA  AGGCTTTAAA                      767

GAGCAATAAA  ATTTTTAGTC  TGCAAAAAAA                                                          797
```

( 2 ) INFORMATION FOR SEQ ID NO:2:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Pro  Pro  Met  Ala  Leu  Pro  Ser  Val  Ser  Trp  Met  Leu  Leu  Ser
1                   5                   10                  15

Cys  Leu  Met  Leu  Leu  Ser  Gln  Val  Gln  Gly  Glu  Glu  Pro  Gln  Arg  Glu
               20                  25                  30

Leu  Pro  Ser  Ala  Arg  Ile  Arg  Cys  Pro  Lys  Gly  Ser  Lys  Ala  Tyr  Gly
          35                  40                  45

Ser  His  Cys  Tyr  Ala  Leu  Phe  Leu  Ser  Pro  Lys  Ser  Trp  Thr  Asp  Ala
     50                  55                  60

Asp  Leu  Ala  Cys  Gln  Lys  Arg  Pro  Ser  Gly  Asn  Leu  Val  Ser  Val  Leu
65                  70                  75                          80

Ser  Gly  Ala  Glu  Gly  Ser  Phe  Val  Ser  Ser  Leu  Val  Lys  Ser  Ile  Gly
               85                  90                      95

Asn  Ser  Tyr  Ser  Tyr  Val  Trp  Ile  Gly  Leu  His  Asp  Pro  Thr  Gln  Gly
               100                 105                 110

Thr  Glu  Pro  Asn  Gly  Glu  Gly  Trp  Glu  Trp  Ser  Ser  Ser  Asp  Val  Met
               115                 120                 125

Asn  Tyr  Phe  Ala  Trp  Glu  Arg  Asn  Pro  Ser  Thr  Ile  Ser  Ser  Pro  Gly
     130                 135                 140

His  Cys  Ala  Ser  Leu  Ser  Arg  Ser  Thr  Ala  Phe  Leu  Arg  Trp  Lys  Asp
145                 150                 155                      160

Tyr  Asn  Cys  Asn  Val  Arg  Leu  Pro  Tyr  Val  Cys  Lys  Phe  Thr  Asp
                    165                 170                 175
```

DETECTION OF PANCREATITIS-ASSOCIATED PROTEIN FOR SCREENING FOR CYSTIC FIBROSIS

BACKGROUND OF THE INVENTION

The human pancreatitis-associated protein (PAP) was isolated, purified and characterized in man and described in the PCT patent application published on 31 Oct. 1991 under the No 91/16428. In the earlier application the PAP was suggested as a means for the detection of a specific disease, acute pancreatitis.

Mucoviscidosis, also called "cystic fibrosis" in English is a very frequent genetic disease in certain populations, which is characterized by a global insufficiency of exocrine secretions of the pancreas and the lung and the exocrine glands in general. Clinically, the disease is associated with abnormally viscous secretions, the mucus formed being capable of obstructing the bronchi and causing serious or mortal disorders.

The mucoviscidosis gene has been localized on human chromosome 7. This gene, called the CFTR gene ("cystic fibrosis transmembrane conductance regulator") shows mutations in different regions in the subjects suffering from mucoviscidosis. Mutations of the same type may be detected on only one of the two chromosomes 7 in subjects called "carriers" but not showing clinical signs of the disease. These persons are heterozygous for the mutation in the CFTR gene.

In the case of a heterozygous mutation, the carrier subject may however suffer certain disorders characteristic of an impairment of the secretory glands. The carrier subject may for example suffer from disorders of the pancreas.

The diagnosis of mucoviscidosis was conducted in the first instance by a test called the "sweat test" which consists of determining the chloride and sodium ions in the sweat of subjects, in particular of children, likely to suffer from this disease. It was possible to correlate the indication of a chloride ion level situated between 60 and 180 mEq/l with the disease in as much as this level is about 40 mEq/l in the normal infant.

Several other types of tests have been successively suggested (Berry, H. K. et al., Am. J. Dis. Child. 1980 134: 930; Crossley, J. R. et al., Lancet 1977 ii: 1093; Forrest, D. C. et al. Arch. Dis. Child. 1981 56 156; Green, M. N. et al., Pediatrics 1968 41: 989; Robinson, P. G. et al., Arch. Dis. Child 1976 51: 301; Schwachman, H. et al., Pediatrics 1949 4: 222), but only the serum determination of trypsin in the newborn (Farriaux J. P. et al., Immunoanal. Biol. Spec. 1992 33: 71) has shown sufficient relevance to still be in force in some countries (Farrell, P. M. et al., Ped. Pulmonol. 1991 supplement 7: 11). This radioimmunological determination is performed on bloodstains deposited on cardboard, the blood being taken from newborn infants for the purposes of screening for other genetic diseases at present screened systematically, phenylketonuria and hypothyroidism. The screening by serum trypsin nonetheless remains very imperfect since the results of a large scale French evaluation program have recently led the French Screening Association not to make it compulsory (Farriaux, J. P. et al. Immunoanal. Biol. Spec. 1992 33: 71).

The principal problem posed by the determination of trypsin in serum is that of false positives (about 1% of the population whereas the incidence of the disease in France is about 0.03% (Farriaux, J. P. et al. Immunoanal. Biol. Spec. 1992 33: 71).

SUMMARY OF THE INVENTION

The inventors have at present demonstrated that the genetic anomalies likely to give rise to disorders characteristic of mucoviscidosis may be reliably correlated in man with an abnormal expression of the PAP from birth.

The object of the present application is the detection of mucoviscidosis or of a mutation in the gene responsible for mucoviscidosis associated with a pancreatic disease by means of a determination of the PAP (pancreatitis-associated protein).

The invention suggests novel agents for carrying out a test for the detection of mucoviscidosis or of a disease of certain exocrine glands, of the pancreas in particular, a disease linked to the existence of a heterozygous mutation in the CFTR gene.

The agents of the invention make it possible to significantly correct the disadvantages shown by the tests known hitherto and in particular these agents offer the possibility of considerably diminishing, even statistically abolishing, the number of false positive results.

The possibility of detecting mucoviscidosis or a pancreatic disease resulting from a mutation in the CFTR gene as a result of assaying for the PAP has made possible the development of a test capable of being used in a neonatal screening or in a screening in children or in adults for mucoviscidosis.

This test may also be performed for the purpose of monitoring the progress of the disease, for example to determine the progress of the pancreatic disease.

Such a test may also be used to detect the presence of a heterozygous mutated CFTR gene not leading to the appearance of a mucoviscidosis but likely to be correlated with a disease of the pancreas in an adult or child patient.

Thus the object of the invention is a procedure for the in vitro detection of a pancreatic disease associated with an impairment of the CFTR gene, characterized in that the concentration of human PAP is determined in a biological sample.

The invention also relates to a procedure for the in vitro detection of mucoviscidosis in a biological sample, characterized in that a determination is made of the concentration of PAP.

The value of the concentration obtained may then be compared with a value which would be obtained under the same test conditions, in the absence of any disease or in the absence of a heterozygous mutation in the CFTR gene.

The inventors have observed that in a disease such as mucoviscidosis, which is not necessarily associated, in particular in the infant, with an acute pancreatitis even in the case of pancreatic insufficiency, a significant, even considerable increase of the PAP level is noted compared with the normal value. This increase may be 2 to 3 times the normal value, and up to 100 times this value. The normal value is determined by reference to the median as defined below.

The suggested determination of the PAP concentration in a biological sample as an indication of an impairment of the CFTR gene associated with a pancreatic disease or a mucoviscidosis offers the advantage of being usable in the framework of neonatal diagnosis In spite of the known and non-pathological phenomenon of transient passage of certain enzymes into the blood at the time of birth, the determination of the PAP remains in fact statistically reliable for detecting mucoviscidosis or a heterozygous mutation in the CFTR gene associated with a pancreatic disease. In other words, when the level of PAP measured in a biological sample, and in particular in the blood, as part of a neonatal test, is abnormal it is possible to deduce from it an anomaly in the CFTR gene associated with mucoviscidosis or in certain cases a pancreatic impairment. The inventors have thus observed that the presence of an abnormally high level of PAP in the blood during a neonatal test can not be confused with the secretion of the enzymes in the blood which may accompany the phenomena of "perinatal stress".

By the expression "abnormally high level" of PAP is meant a value of PAP more than twice, for example, the median value calculated from the PAP level determined in a group of reference samples.

According to a first embodiment of the invention, the in vitro detection procedure for mucoviscidosis or for a mutation heterozygous for the CFTR gene accompanied by a pancreatic disease is characterized by:

the determination of the PAP concentration in a biological sample, the comparison of the value obtained with the median value calculated for a defined group of reference samples previously subjected to the PAP determination under the same conditions.

By "group of reference samples" is preferably meant samples obtained from patients not homozygous for the mutation in the CFTR gene.

The median in question above is the value of the measurement obtained for a given sample and chosen such that there exists an equal number of observations (measurements) above and below this value in the defined group of samples tested. When the number of measurements performed is even, the median is indeterminate between the two central values observed.

An advantageous embodiment of the invention is also characterized in that the determination of the serum concentration of PAP comprises:

the placing of a biological sample, for example blood or serum, in contact with antibodies recognizing human PAP, the detection of the formation of an immunological complex of the PAP-antibody type, the determination of the PAP-antibody complex.

The antibodies used for carrying out this determination may be polyclonal or monoclonal antibodies, even both of these types of antibodies when the test is an immunological assay of the sandwich type.

Preferably the antibody forming the immunological complex with the PAP is a monoclonal antibody. Advantageously, it is a monoclonal antibody specific for human PAP which consequently does not show an immunological reaction with the constituents present in a normal biological sample and in particular in the normal reference blood; in particular, this antibody shows no reaction with the lectins of the blood.

By "normal blood" or "normal sample" is meant a sample containing a very low level of PAP.

It will be of interest in the framework of the embodiment of the in vitro detection test of the invention to select an antibody or antibodies specific for PAP which give rise to a weak background signal (measurable by placing a normal serum or a normal sample in contact with this antibody).

A particularly advantageous procedure for carrying out the invention is characterized in that it comprises the following steps:

the placing of a defined quantity of a biological sample, for example a sample of blood or serum in which PAP is to be assayed in contact with a monoclonal antibody (called "capture antibody") recognizing specifically human PAP under conditions allowing the formation of an immunological complex between the capture antibody and the PAP when it is present in the sample being determined, the placing of the reaction medium obtained in the preceding step in contact with a monoclonal antibody (called "detection antibody") recognizing a different epitope from the epitope recognized by the capture antibody, the detection antibody being labelled under conditions allowing the formation of an immunological complex between the detection antibody and the antigen previously bound to the capture antibody, washing to eliminate the unreacted detection antibodies, the detection of capture antibody-PAP antigen-detection antibody complexes, the determination of the PAP concentration and optionally its comparison with a median calculated for a defined group of reference samples previously subjected to the same determination of PAP under the same conditions.

For carrying out the procedure described above it will be possible to use a capture antibody/detection antibody couple in which the capture antibody will be a polyclonal serum and the detection antibody will be a monoclonal antibody. It is also possible to use a capture antibody/detection antibody couple in which all of the antibodies are monoclonal, it being understood that the capture antibody and the detection antibody recognize distinct epitopes on the PAP.

Quite satisfactory results may also be obtained when the capture antibody is a polyclonal serum and the detection antibody is also a polyclonal serum of the same nature and optionally of the same origin as regards its preparation, this latter being however labelled.

In order to carry out the sandwich-type ELISA assay described above for the PAP, a selection of the monoclonal antibodies and/or polyclonal sera must be made, in the knowledge that the capture antibody is to be used to coat the wells of a microtitration plate.

In the selection of these antibodies the specialist skilled in the art will allow for the fact that the absorption of an antibody to a solid support may lead to a loss of activity owing to conformational changes in the molecule. Thus, it will be necessary to check in the first instance that the antibody or serum selected is capable of recognizing the natural PAP and/or recombinant PAP after having been bound to a support.

The specialist skilled in the art will also be able to select a monoclonal detection antibody recognizing a different epitope on the PAP from the epitope recognized by the capture antibody by carrying out for example a detection test for the PAP by competition between the two antibodies selected.

Generally, the capture antibody/detection antibody couple or the polyclonal serum used both for capture and detection must exhibit a satisfactory sensitivity as well as permit a good reproducibility of the results and a good stability over time (about 6 months for antibodies stored at 4° C.).

Thus, a monoclonal capture antibody designated 6F3E4, produced by the hybridoma deposited with the ECACC (European Collection of Animal Cell Cultures, Portan down, Salisbury, Wiltshire SP4 OJG, Great Britain) under No 92122310 on 23 Dec. 1992, is advantageously used. Similarly, a particularly useful detection antibody is the antibody 16F4B8 produced by the hybridoma deposited with the ECACC under No. 92122309 on December 1992.

The detection antibody or the polyclonal serum should be labelled with any appropriate label in order to make possible the detection of the capture antibody-PAP antigen-detection antibody complex formed during the detection test. As an indication, it will be possible to use radioactive labels or even enzymatic markers. As an example, mention may be made of labelling with the aid of horseradish peroxidase.

The detection procedure mentioned above making use of antibodies may be modified such that the capture antibody and/or the detection antibody are replaced by their variable fragments or a part of these variable fragments. As an example, it is possible to use F(ab')$_2$ or Fab fragments to carry out the reaction.

Moreover, the invention relates to a monoclonal antibody, characterized in that it recognizes the recombinant and/or purified natural human PAP when it is adsorbed to a solid support.

The PAP has been described in the PCT application previously mentioned; its nucleotide sequence and its amino acid sequence are reported in FIG. 3.

Advantageous antibodies complying with these conditions are the antibodies 6F3E4 or 16F4B8 described above.

Finally, the object of the invention is a kit containing at least two monoclonal antibodies directed specifically against different epitopes of the human PAP, at least one of these monoclonal antibodies (capture antibody) recognizing the human PAP when it is bound to a solid support.

Generally, the invention relates to the use of monoclonal antibodies recognizing specifically the human PAP for the in vitro detection of mucoviscidosis, or a pancreatic disease linked to a mutation heterozygous for the CFTR gene.

Also included in the framework of the invention is a kit for the in vitro detection of mucoviscidosis or a pancreatic disease associated with a mutation heterozygous for the CFTR gene containing:

monoclonal or polyclonal antibodies described above, one of these antibodies (detection antibody) being labelled, a reagent making it possible to reveal the detection antibody, a negative control.

A preferred kit for carrying out the invention contains as capture antibody the antibody 6F3E4 and as detection antibody the antibody 16F4B8.

A particularly useful kit contains a polyclonal serum for the detection of the PAP. A part of this serum is to be used for the capture of the PAP, the other part contains labelled antibodies for the detection in a sandwich-type assay of the presence of a complex of the PAP-antibody type.

The appropriate polygonal sera may be prepared in animals, for example rabbits, to which the purified PAP is administered.

A useful kit thus contains:

a polyclonal serum recognizing the human PAP, optionally a polyclonal serum recognizing the human PAP, the antibodies of which are labelled, a reagent making it possible to reveal the labelled antibodies, a negative control.

The invention also relates to the hybridoma producing the antibody 6F3E4 identified by the No. 92122310 at the ECACC as well as the hybridoma producing the antibody 16F4B8 identified by the No. 92122309 at the ECACC.

Other characteristics and advantages of the invention will become apparent in the Examples and in the Figures which follow.

Result of a determination of serum PAP by means of a competitive ELISA-type assay making use of polyclonal antibodies obtained from the rabbit and recognizing the purified human PAP. This determination was carried out in patients suffering from mucoviscidosis.

FIG. 2

Determination of PAP in the newborn infant.

FIG. 3

Nucleotide and amino acid sequences of human PAP.

DETAILED DESCRIPTION OF THE INVENTION

EXAMPLE 1

EXPERIMENTAL DETERMINATION

1—Determination of PAP in patients suffering from mucoviscidosis

Protocol: Blood samples taken from 66 patients aged from 15 days to 40 years in whom the diagnosis of mucoviscidosis had been confirmed by the sweat test (Shwachman H. et al., Ann. N.Y. Acad. Sci. 1962 93: 600) and/or genetic analysis (Collins F. S. Cystic fibrosis: Molecular biology and therapeutic implications. Science 1992 256: 774) were analyzed. A series of healthy individuals of corresponding ages was studied in parallel. The PAP was determined in these samples by using the following determination:

Determination of serum PAP: This determination, of the competitive ELISA type, uses polyclonal antibodies obtained from the rabbit by repeated injections of purified human PAP (Keim V. et al., Gastroenterology 1992 103: 248). Proteins of human pancreatic juice containing PAP were adsorbed onto microtitration plates (100 ng of proteins by wells). The serum sample (50 $\mu$l) is placed in an Eppendorf tube in the presence of 0.5 $\mu$l of immune serum and incubated in a final volume of 100 $\mu$l of 100 mM Tris pH 7.4, 1% TWEEN 20, 1.5% bovine serum albumin for 2 h at room temperature. (TWEEN 20 is polyethoxyethylene sorbitan monolaurate.) The mixture is then loaded into a microtitration well treated as described above and incubated for 2 h at room temperature. The well is then rinsed three times with 300 $\mu$l of PBS containing 0.5% of TWEEN 20. The detection is done with the aid of goat anti-rabbit immunoglobulin antibody, labelled with peroxidase (100 $\mu$l) to 0.2 $\mu$g/ml). The reference curve is established using purified PAP.

Figure 1:
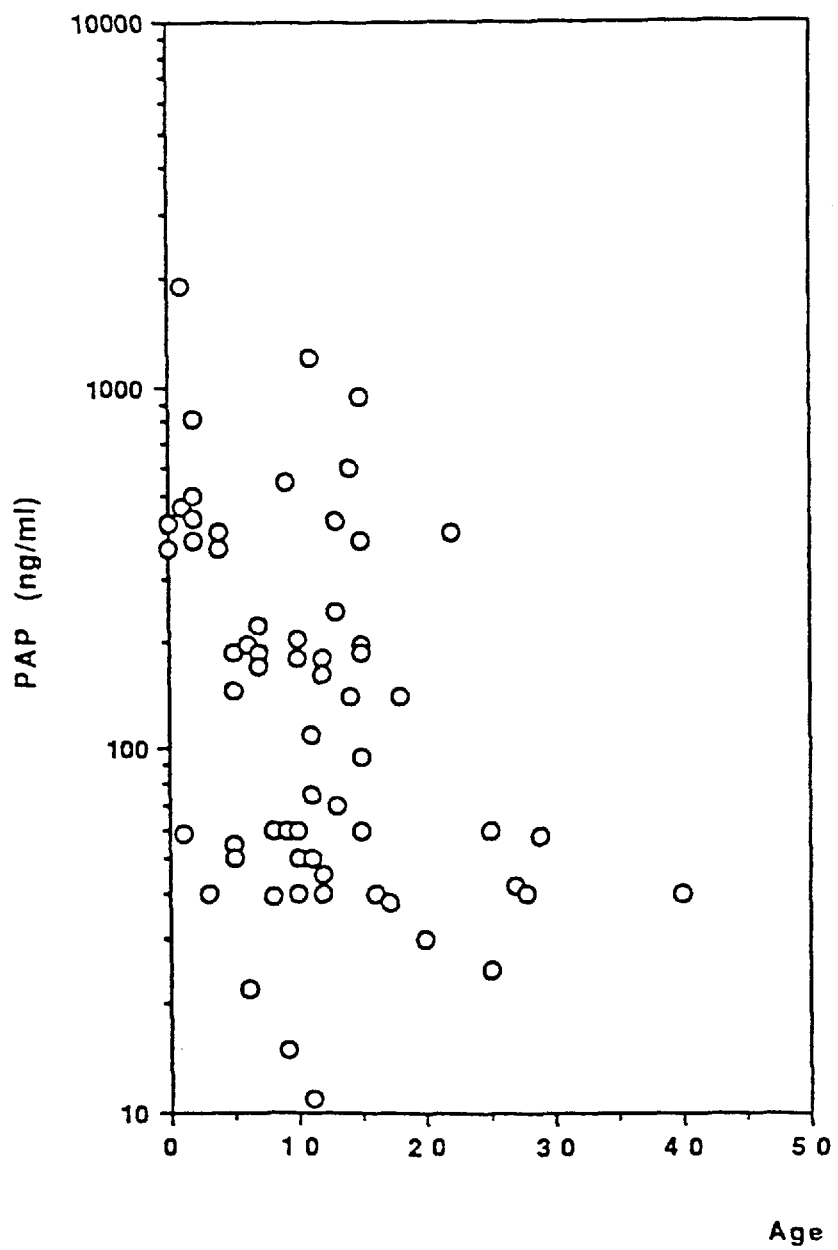
FIG. 1

Results: The results shown in FIG. 1 show that:

in patients suffering from mucoviscidosis the serum concentration of PAP is always higher than that of the controls. The values of the controls range from 1 to 10 ng/ml, those of the patients between 11 and 1900 ng/ml.

The highest values are observed in the youngest patients.

2. Determination of PAP in the newborn: The pathological anatomy analysis of foetuses suffering from mucoviscidosis showed a pancreatic disease in all cases (Boué A. et al., Hum. Genet. 1988, 74: 288). The inventors deduced from this that the concentration of PAP is already likely to be elevated in the blood of newborn infants suffering from mucoviscidosis.

Protocol: This could be demonstrated by the following experiment:

The determination of PAP was carried out on cardboard strips obtained from screening centres bearing dried blood samples. The cardboard strips corresponded to four groups of individuals: Group 1: Controls (normal trypsin at birth) (n=50) Groups 2, 3 and 4: children showing a high trypsin at birth.

Group 2: "false-positive" children (no anomaly of the CFTR gene, negative sweat test) (n=60).

Group 3: children heterozygous for the mutated CFTR gene (not affected), negative sweat test (n=33).

Group 4: children suffering from mucoviscidosis (homozygous for the mutated CFTR gene, sweat test positive) (n=11).

Determination: the determination was carried out as follows: The blood deposits on the cardboard strips used were less than two months old. The cardboard strips corresponded to the standards defined by the French Screening Association. A disk 6 mm in diameter was cut out from each cardboard strip at the site of the blood stain. The corresponding quantity of blood is about 10 µl. Each disk was deposited in an Eppendorf tube of 1.5 ml total volume containing 150 µl of a 100 mM Tris solution, pH 7.4, 1% TWEEN 20, 1.5% bovine serum albumin and shaken an a Multivortexer mixer (Amersham France S.A.) for 8 h at room temperature. The entire solution containing the desorbed blood is added to 50 µl of Tris solution pH 7.4, 1% TWEEN 20, 1.5% bovine serum albumin containing 0.5 µl anti-PAP antiserum (total volume 200 µl) and incubated for 2 h at room temperature. The subsequent part of the determination is carried out exactly as described above.

Results

Figure 2:
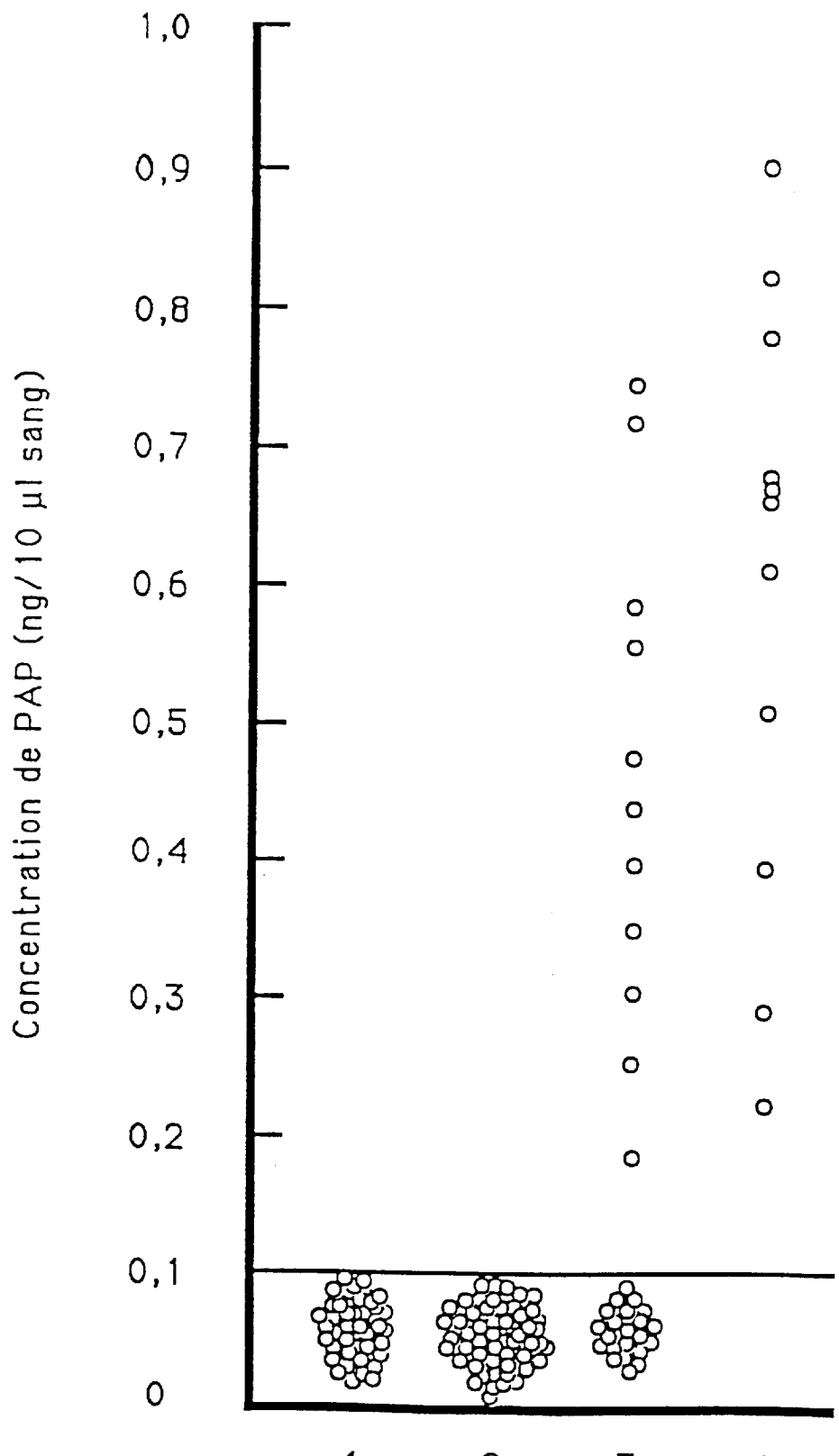

The results shown in FIG. 2 may be summarized as follows:
1) The children having a negative trypsin (controls, group 1) have a serum PAP concentration included between 0.01 and 0.1 ng/10 µl of blood (median 0.065).
2) The children of group 2 (trypsin positive but not diseased) show the same values as the controls.
3) A third (11/33) of the children of group 3 (heterozygotes) showed a PAP serum concentration ranging from 0.18 to 0.75 ng/ml of blood.
4) All of the children suffering from mucoviscidosis (11/11) showed a PAP serum concentration ranging from 0.22 to 0.90 ng/10 µl of blood;

Conclusion

1) None of the control children showed a PAP concentration in the blood higher than 0.1 ng/10 µl of blood. This experiment shows that every value twice as high (higher than 0.11 ng/10 µl of blood) as the median is abnormal.
2) Moreover, all of the children suffering from mucoviscidosis showed PAP values in the blood higher than this threshold.
3) Contrary to the system based on the determination of trypsin, the determination of PAP seems only to select the children having mucoviscidosis and those heterozygous for the impaired gene whose pancreatic disease is the most pronounced.

The test proposed hence shows the required properties for its use in neonatal screening of mucoviscidosis.

EXAMPLE 2

INDUSTRIAL DETERMINATION

1. With the aid of monoclonal antibodies

The development of a "sandwich"-type ELISA assay for PAP has made it necessary to select two monoclonal antibodies recognizing two different epitopes on the antigen:
one to be used to coat the wells of a microtitration plate (capture antibody),
the other coupled to an enzyme destined to reveal the antigen adsorbed to the wells (detection antibody).

This selection was made with monoclonal antibodies produced in ascites and purified by affinity chromatography on a protein A-SEPHAROSE column in the case of the IgG or on an immunoadsorbent column in the case of the IgM (rat anti-mouse IgM monoclonal antibody coupled to a SEPHAROSE matrix; SEPHAROSE is agarose beads).

The adsorption of an immunoglobulin to a solid support results in conformational changes which may lead to a loss of activity of the molecule. All of the anti-PAP monoclonal antibodies obtained in the laboratory have thus first to be tested for their capacity after adsorption to microtitration plates (NUNC MAXISORP) to recognize natural and recombinant PAP. After incubation, the antigen-antibody complexes were revealed with the aid of Fab fragments of anti-PAP rabbit immunoglobulins conjugated to peroxidase, using o-phenylenediamine as enzyme substrate.

All of the immunoglobulins having conserved this capacity were selected as potential capture antibodies and coupled to biotin.

These biotinylated antibodies were used in competition assays to select a detection monoclonal antibody.

These assays were carried out with (natural and recombinant) PAP adsorbed to wells of microtitration plates coated with rabbit anti-PAP IgG. The binding of the biotinylated monoclonal antibodies to the antigen (revealed with the aid of an avidin-POD complex) was measured in the absence or in the presence of an excess of the different monoclonal antibodies to be assayed.

All of the monoclonal antibodies not competing with at least one of the biotinylated antibodies (and hence recognizing a different epitope) were selected as potential detection antibodies.

They were then coupled to POD in the form of the Fab' fragment before being used for the development of the final form of the ELISA assay for the determination of PAP.

This development has made it necessary to investigate which capture antibody-detection antibody couple would produce the highest sensitivity in the test, the best reproducibility of the results and the greatest stability of the reagents with time.

Two monoclonal antibodies complied with all of these selection criteria:

the antibody 6F3E4 used for capture the antibody 16F4B8 used for detection.

2. With the aid of polyclonal sera

A sandwich type ELISA PAP determination adapted to the conditions of screening was developed. Its characteristics are the following:

Production of the Antibodies

The antigen was the human PAP highly purified according to the following procedure: from transplanted pancreatic juice, lyophilized, a first separation by ion exchange chromatography (HPLC, MonoS column) made it possible to isolate a peak containing the PAP and a high molecular weight contaminant. This peak was then resolved by molecular sieving (HPLC, SEPHACRYL 200 HR column, SEPHARCRYL is acrylamide bonds). The PAP was then recovered in the form of a homogeneous fraction. The control carried out by SDS-gel electrophoresis and staining with silver made it possible to ensure a purity of more than 98%.

The immunization was carried out according to the usual laboratory procedure described by V. Keim et al. (Gastroenterology, 1992 103: 248).

The quality of the immune sera was assayed by use of serial dilutions in Western blots.

Construction of the ELISA

It is a polyclonal/polyclonal sandwich ELISA.

The immunoglobulins of the immune serum were purified by means of a protein A-SEPHAROSE affinity column.

The immunoglobulins intended for detection were labelled with biotin according to the usual procedure known to the specialist. The system of detection implicated avidin POD.

The sensitivity of the assay is 50 pg/ml.

Results obtained:

Forty samples from newborn infants were tested on cardboard strips. The PAP concentrations were all less than 60 pg/ml. One infant suffering from mucoviscidosis had a value of 800 pg/ml. Six children (aged between 3 months and 10 years) suffering from the disease and whose blood had also been sampled on cardboard, showed values ranging from 0.5 ng/ml to 1.8 ng/ml.

These results confirm the differences already observed with the determination carried out with the monoclonal antibodies.

---

What is claimed is:

1. A method for screening for cystic fibrosis, comprising determining the concentration of human pancreatitis-associated protein in a biological sample from a patient, wherein finding a concentration of human pancreatitis-associated protein that is higher than a median human pancreatitis-associated protein concentration in healthy individuals indicates a positive screen for cystic fibrosis.

2. The method of claim 1, wherein the determining of the concentration of said human pancreatitis-associated protein comprises:
    i) contacting said biological sample with at least one antibody that specifically binds to said human pancreatitis-associated protein,
    ii) detecting the formation of a complex of said at least one antibody and said human pancreatitis-associated protein, and iii) determining the amount of the pancreatitis-associated protein-antibody complex formed.

3. The method according to claim 2, wherein the detecting step ii) is performed by a sandwich immunoassay using a polyclonal capture antibody and a monoclonal detection antibody.

4. The method according to claim 3, wherein the detection antibody is produced by hybridoma ECACC 92122309.

5. The method according to claim 3, wherein the detection antibody is labeled with horseradish peroxidase.

6. The method according to claim 3, wherein the capture antibody is coupled to biotin in order to immobilize said capture antibody.

7. The method according to claim 6, wherein the detection antibody is labeled with horseradish peroxidase.

8. The method of claim 2, wherein said patient is a neonate, said biological sample is a blood sample; and said median pancreatitis-associated protein concentration is 0.1 ng/10 µl.

9. The method of claim 2, wherein said at least one antibody is a monoclonal antibody.

10. The method according to claim 2, wherein the detecting step ii) is performed by a sandwich immunoassay using a monoclonal capture antibody and a monclonal detection antibody.

11. The method according to claim 10, wherein the detection antibody is labeled with horseradish peroxidase.

12. The method according to claim 11, wherein the capture antibody is produced by hybridoma ECACC 92122310.

13. The method according to claim 11, wherein the detection antibody is produced by hybridoma ECACC 92122309.

14. The method according to claim 10 wherein the capture antibody is coupled to biotin in order to immobilize said capture antibody.

15. The method according to claim 14, wherein the detection antibody is produced by hybridoma ECACC 92122309.

16. The method according to claim 10, wherein the capture antibody is produced by hybridoma ECACC 92122310.

17. The method according to claim 16, wherein the detection antibody is produced by hybridoma ECACC 92122309.

18. The method according to claim 10, wherein the detection antibody is produced by hybridoma ECACC 92122309.

19. The method according to claim 1, wherein a concentration of said human pancreatitis-associated protein in said biological sample at least two times the median concentration from healthy individuals indicates a positive screen for cystic fibrosis.

20. The method according to claim 1, wherein a concentration of said human pancreatitits-associated protein in said biological sample above 10 ng/ml indicates a positive screen for cystic fibrosis.

21. The method according to claim 1, wherein said patient is a neonate.

22. The method according to claim 2, wherein said detecting step ii) is performed by a sandwich immunoassay using a monoclonal capture antibody and a polyclonal detection antibody.

23. An immunoassay for quantitating human pancreatitis-associated protein that comprises:
   i) contacting a sample to be assayed with a monoclonal antibody to form a complex between said monoclonal antibody and said human pancreatitis-associated protein;
   ii) determining the amount of said human pancreatitis-associated protein in said sample by determining the amount of said complex formed;
wherein said monoclonal antibody is produced by hybridoma ECACC 92122310 or hybridoma ECACC 92122309.

24. The immunoassay according to claim 23, wherein said monoclonal antibody is labeled with biotin or with horseradish peroxidase.

25. An immunoassay for quantitating human pancreatitis-associated protein that comprises:
   i) contacting a sample to be assayed from a human with an immobilized antibody to form an immobilized complex between said monoclonal antibody and said human pancreatitis-associated protein;
   ii) contacting the complex formed in step i) with a second monoclonal antibody to form an immobilized tertiary complex; and
   iii) determining the amount of said human pancreatitis-associated protein in said sample by determining the amount of said tertiary complex formed;
wherein said second monoclonal antibody is produced by a ECACC 92122310 or by hybridoma ECACC 92122309.

26. The method of claim 25, wherein said immobilized antibody is a polyclonal antibody.

27. The method of claim 25, wherein said immobilized antibody is a monoclonal antibody.

28. The method of claim 27, wherein said immobilized monoclonal antibody is the monoclonal antibody produced by the hybridoma ECACC 92122310 and wherein said second monoclonal antibody is the monoclonal antibody produced by the hybridoma ECACC 92122309.

29. The method of claim 25, wherein said human is a neonate and said sample is a blood sample.

30. A monoclonal antibody produced by hybridoma ECACC 92122309.

31. The monoclonal antibody according to claim 30 that is immobilized or that is labeled with biotin.

32. A monoclonal antibody produced by hybridoma ECACC 92122310.

33. The monoclonal antibody according to claim 32 that is immobilized or that is labeled with biotin.

34. Hybridoma ECACC 92122309.

35. Hybridoma ECACC 92122310.

* * * * *